United States Patent [19]

Miller

[11] 4,175,208
[45] Nov. 20, 1979

[54] PROCESS FOR THE PREPARATION OF 1-CHLORO-2-HYDROXY-3-NAPHTHOIC ACID

[75] Inventor: Frank Miller, Bridgewater, N.J.

[73] Assignee: American Cyanamid Company, Stamford, Conn.

[21] Appl. No.: 1,568

[22] Filed: Jan. 5, 1979

[51] Int. Cl.$^2$ .............................................. C07C 69/76
[52] U.S. Cl. ................................................... 562/467
[58] Field of Search ........................................ 562/467

[56] References Cited

PUBLICATIONS

Gandbhir, A. M. et al., Chem. Abstracts 46:482 1952.

*Primary Examiner*—Paul J. Killos
*Attorney, Agent, or Firm*—Bruce F. Jacobs

[57] ABSTRACT

1-Chloro-2-hydroxy-3-naphthoic acid is prepared by chlorination using an alkali metal or alkaline earth metal hypochlorite. The compound is useful as a dye modifier.

3 Claims, No Drawings

PROCESS FOR THE PREPARATION OF 1-CHLORO-2-HYDROXY-3-NAPHTHOIC ACID

The present invention relates to the preparation of 1-chloro-2-hydroxy-3-naphthoic acid and, more particularly, to a process for the chlorination of 2-hydroxy-3-naphthoic acid using an alkali metal or alkaline earth metal hypochlorite.

1-Chloro-2-hydroxy-3-naphthoic acid is a useful modifier compound, in combination with 2-hydroxy-3-naphthoic acid, in the preparation of azo pigments whereby an aromatic aminosulfonic acid is diazotized and coupled into a mixture of 2-hydroxy-3-naphthoic acid and its 1-chloro derivative, as is disclosed in co-filed, commonly assigned application, serial number The preparation of 1-chloro-2-hydroxy-3-naphthoic acid for the above-stated use, and others, by conventional methods for chlorination of phenolic compounds has been found to be unsatisfactory. Such methods as direct chlorination with chlorine gas in an anhydrous solvent, such as glacial acetic acid, carbon tetrachloride, etc., or in the absence of a solvent, or chlorination with sulfuryl chloride, are described by Migrdichian, Organic Synthesis, Vol. II, Reinhold Publishers, N.Y. 1957.

The process of the present invention provides 1-chloro-2-hydroxy-3-naphthoic acid in high yields of high purity material and poses no significant environmental problems or difficult solvent recovery.

According to the present invention, 2-hydroxy-3-naphthoic acid is chlorinated as the dialkali metal salt thereof, preferably the disodium salt, prepared by dissolving the compound in at least about 2 moles of alkali metal hydroxide solution per mole thereof, to provide an aqueous alkaline solution of the dialkali metal salt. Sodium hydroxide is preferred. Preferably, the compound is dissolved in excess alkali metal hydroxide solution, e.g., about 3 moles per mole thereof.

This solution, at a temperature up to about 70° C., preferably below about 25° C., is then contacted with an aqueous solution of an alkali metal or alkaline earth metal hypochlorite. The amount of hypochlorite used will range from about 0.7 to 2.5 moles per mole of the dialkali metal salt, preferably about 1.0–1.3 moles per mole thereof.

When the hypochlorite has been added, the resulting reaction mixture is heated, preferably at the boil, to permit ease of filtration, and then cooled and acidified with an inorganic acid, e.g., hydrochloric acid, to precipitate the desired 1-chloro compound. The product is filtered, washed with water, and dried.

EXAMPLE 1

Preparation of 1-Chloro-2-Hydroxy-3-Naphthoic Acid

A solution of 47.4 grams of 2-hydroxy-3-naphthoic acid (99.3% purity) is added to a hot (80° C.) solution of 60 grams of 50% sodium hydroxide and 300 ml water. The solution is heated to boiling to dissolve all the 2-hydroxy-3-naphthoic acid and then allowed to cool to 3° C. in an ice bath. The solution contains 0.25 mole of 2-hydroxy-3-naphthoic acid and 0.75 mole sodium hydroxide.

A second solution, containing 0.275 mole of sodium hypochlorite is obtained by mixing 133.5 grams of a solution of 15.33% sodium hypochlorite with 137 ml water. This solution is cooled to 3° C.

The chilled sodium hypochlorite solution is added to the chilled solution of 2-hydroxy-3-naphthoic acid, keeping the temperature below 10° C. When the addition of sodium hypochlorite is completed, the reaction mixture is held at about 10° C. for 2 hours and then heated to the boil. To this solution is then added 250 ml of 14.1% hydrochloric acid. The resulting slurry of deep yellow solid material is heated to the boil and then cooled to ambient temperature. The slurry is filtered, washed with 2 liters of water and dried to constant weight. There is obtained 52.6 grams of 1-chloro-2-hydroxy-3-naphthoic acid (purity 97.2% by HPLC) representing a yield of 91.8% of theoretical.

What is claimed is:

1. A process for the preparation of 1-chloro-2-hydroxy-3-naphthoic acid which comprises reacting, at a temperature below about 70° C., and aqueous alkaline solution of the dialkali metal salt of 2-hydroxy-3-naphthoic acid, containing at least 2 moles of an alkali metal hydroxide per mole of said 2-hydroxy-3-naphthoic acid, with an aqueous solution containing about 0.7 to 2.5 moles of an alkali or alkaline earth metal hypochlorite per mole of said dialkali metal salt.

2. A process according to claim 1 wherein said reaction is conducted at a temperature below 25° C. and wherein the dialkali metal salt is the disodium salt of 2-hydroxy-3-naphthoic acid and the alkali metal hypochlorite is sodium hypochlorite.

3. A process according to claim 2 wherein about 3–4 moles of sodium hydroxide and about 1–1.3 moles of sodium hypochlorite are used.